(12) United States Patent
Osman et al.

(10) Patent No.: US 6,451,196 B1
(45) Date of Patent: Sep. 17, 2002

(54) IONIC RESERVOIR THROUGH APPLICATION OF AN ELECTRICAL POTENTIAL

(75) Inventors: Peter Damien John Osman, West Lindfield; Burkhard Raguse, New South Wales; Lech Wieczorek, North Ryde, all of (AU)

(73) Assignees: Australian Membrane and Biotechnology Research Institute, Chattsworth (AU); The University of Sydney, Sydney (AU)

( * ) Notice: Subject to any disclaimer, the term of this patent is extended or adjusted under 35 U.S.C. 154(b) by 0 days.

(21) Appl. No.: 08/952,419

(22) PCT Filed: May 17, 1996

(86) PCT No.: PCT/AU96/00304

§ 371 (c)(1),
(2), (4) Date: Jan. 4, 1999

(87) PCT Pub. No.: WO96/36871

PCT Pub. Date: Mar. 21, 1996

(30) Foreign Application Priority Data

May 17, 1995 (AU) .............................................. PN 3031

(51) Int. Cl.[7] .............................................. G01N 27/33
(52) U.S. Cl. ............. 205/789; 204/403.06; 204/403.08; 204/418; 205/778; 205/793; 205/777.5
(58) Field of Search ................................. 204/403, 415, 204/418; 205/777.5, 778, 793, 789

(56) References Cited

U.S. PATENT DOCUMENTS

| 5,328,847 A | * | 7/1994 | Case et al. ................... 205/778 |
| 5,368,712 A | | 11/1994 | Tomich et al. .............. 204/403 |

FOREIGN PATENT DOCUMENTS

| AU | WO 8700168 | 1/1987 |
| WO | WO-9217788 A1 | * 10/1992 |

* cited by examiner

*Primary Examiner*—Jill Warden
*Assistant Examiner*—Alexander Stephan Noguerola

(57) ABSTRACT

An improved membrane based biosensor incorporates sensing and reference electrodes and a dc electrical potential produced by a counter electrode. The biosensor incorporates ionophores. The conductivity of the membrane is dependent on the presence or absence of an analyte. A functional reservoir exists between the sensing electrode and a lipid membrane deposited on the sensing electrode. The invention also includes the method of detecting the presence or absence of the analyte by use of the biosensor.

34 Claims, 19 Drawing Sheets

Linker Lipid

Linker Gramicidin $n = 0, 1, 2, 3, 4, 5, 6, 7, 8$

Biotinylated gramicidin

GDPE

DPEPC

IONIC RESERVOIR THROUGH APPLICATION OF AN ELECTRICAL POTENTIAL

The present invention relates to an improved membrane based biosensor and to a method of improving the performance of membrane based biosensors.

Biosensors based on ion channels or ionophores contained within lipid membranes that are deposited onto metal electrodes, where the ion channels are switched in the presence of analyte molecules have been described in International Patent Application Nos. WO 92/17788, WO 93/215289, WO 94/07593 and U.S. Pat. No. 5,204,239 (the disclosures of which are incorporated herein by reference). As these biosensors rely on changes in ion conduction through the membrane, usually mediated by an ionophore, it is important that there exists an ionic reservoir between the electrode and the lipid membrane. Ideally this ionic reservoir between the electrode and the lipid reservoir is not totally depleted or filled, by conduction through the ionophore, during the course of the measurement cycle. The usual method of measuring the conductance changes is the use of alternating current (AC) impedance spectroscopy. The abovementioned disclosures have shown that good reservoirs can be produced using special linker lipid compounds.

The present inventors have now found that the application of a direct current (dc) potential offset superimposed onto the AC impedance signal can influence the apparent conduction of ions by the ionophore through the membrane. Without wishing to be bound by scientific theory it is believed that this modification of the ionophore conduction occurs through the modulation of the reservoir capacity and improvement in the reservoir homogeneity. This improvement in conduction of ions by the ionophore therefore allows the use of less ionophore which may be useful in producing more sensitive sensor membranes as less analyte is required to switch the ionophore on/off. A negative dc potential applied to the metal electrode has been shown to improve the ion conduction by ionophores, whereas a positive dc potential applied to the metal electrode has been shown to decrease and even negate the apparent conduction of the ionophores through the membrane. This effect is especially noticeable when membranes are formed containing phosphatidyl choline based lipids. The inventor has found that by controlling the dc offset, the reproducibility of the ionophore conduction is greatly improved.

Accordingly, in a first aspect the present invention consists in an improved membrane based biosensor comprising a lipid membrane incorporating ionophores the conductivity of the membrane being dependent on the presence or absence of an analyte, a reference electrode, a sensing electrode onto which is deposited the lipid membrane such that a functional reservoir exists between the lipid membrane and the sensing electrode, the improvement comprising including in the biosensor means to apply a dc electrical potential offset to the sensing electrode relative to the reference electrode.

In a second aspect the present invention consists in an improved method of detecting the presence or absence of an analyte in a sample using a membrane based biosensor comprising a lipid membrane incorporating ionophores the conductivity of the membrane being dependent on the presence or absence of the analyte, a reference electrode, a sensing electrode on to which is deposited the lipid membrane such that a functional reservoir exists between We lipid membrane and the sensing electrode, the improvement comprising applying a dc electrical potential offset to the sensing electrode relative to the reference electrode.

In a third aspect by incorporating ionisable, polarisable, dipolar or otherwise electroactive species within the membrane based biosensor comprising a lipid membrane incorporating ionophores the conductivity of the membrane being dependent on the presence or absence of an analyte. a reference electrode, a sensing electrode onto which is deposited the lipid membrane such that a functional reservoir exists between the lipid membrane and the sensing electrode, the appropriate dc potential can be induced between the sensor electrode and the analyte solution Although it is envisaged that generally it is preferred to apply a negative potential onto the metal sensor electrode in order to improve the ionophore conduction, it may be useful in some circumstances to apply a positive potential onto the metal sensor electrode thus reducing or negating the apparent ionophore conduction through the membrane.

In a preferred embodiment of the present invention a dc potential of between +500 mV to −500 mV is applied to the sensing electrode.

In a further preferred embodiment the dc offset is produced through the use of a counter electrode where the electrochemical potential between the counter electrode and the sensing electrode produces an electrical potential of between 0 to −500 mV, with the sensing electrode being at the negative potential.

In a preferred embodiment the counter electrode is made from stainless steel.

In a further preferred embodiment the counter electrode is made from titanium.

In a further preferred embodiment the counter electrode is made from silver, gold, platinum, palladium, copper, chromium or molybdenum.

In another preferred embodiment the counter electrode is made from metals that are capable of being deposited in a thin film onto a plastic, glass or silicon substrate, said metals being stable for at least 30 minutes in aqueous solution and sets up the appropriate electrochemical potential relative to the sensing electrode on addition of an aqueous solution.

In a further preferred embodiment of the present invention the counter electrode is an electrochemically neutral metal relative to the sensing electrode and the dc electrical potential of between +500 to −500 mV is created by electronic means.

In a further preferred embodiment of the present invention the counter electrode produces an electrochemical potential relative to the sensing electrode which is enhanced or negated or reversed using a dc electrical potential created by electronic means to give a potential of between +500 to−500 mV.

In yet another preferred embodiment of the present invention, the dc offset potential of the sensing electrode, onto which is deposited the lipid membrane, is controlled using a three terminal measurement, where the impedance measurement is made between the counter electrode and the working electrode which is the sensing electrode and where the dc offset potential is controlled by a reference electrode to be between +500 to −500 mV as required.

The metals used for the counter electrode and the reference electrode in the three terminal measurement may be any of the commonly used metals and electrode combinations commonly used in these measurements as known to those skilled in the art.

In a further preferred embodiment of the present invention the metal used for the sensing electrode is a layer of freshly evaporated or sputtered gold. Alternatively, a freshly cleaned gold surface, which can be produced using plasma etching or ion-beam milling, can be used.

It is further preferred that the first layer of the lipid membrane is produced using the linker lipid shown in FIG. 1, the disulfide of mercaptoacetc acid, linker gramicidin shown in FIG. 2, the membrane spanning lipid (C) and the membrane spanning lipid (D) both shown in FIG. 3.

It is further preferred that the second layer of the lipid membrane is produced from diphytanyl phosphatidyl choline, glycerol diphytanyl ether, shown in FIG. 7. and biotinylated gramicidin shown in FIG. 4.

In a further preferred embodiment the second layer lipid contains at least a proportion of a phosphatidyl choline, or phophatidyl ethanolamine or phosphatidic acid lipid.

In a further preferred embodiment the second layer lipid contains at least a proportion of a charged lipid.

In a further preferred embodiment the lipid membrane is a monolayer.

As will be appreciated by those skilled in the art, if the sensing of an analyte occurs through the swing off or on of an ionophore contained within the lipid sensing membrane on addition of nalyte, then it is possible to monitor this change in conduction by measuring the amount of electrical potential required in order to maintain the membrane conduction value at the initial ungated membrane conduction value. The magnitude and sign of the electrical potential is then related to the amount of analyte present in the sample.

By increasing the signal spectral inhomogeneity the information content in the sign can be increased with the consequent possibility of improved signal to noise. One mechanism for achieving this is to take advantage of the system voltage dependence by applying a non sinusoidal excitation and then analyzing the results by fourier transform in which case the signal information content will be increased due to the cross modulation products in the output.

By automatically selecting a dc potential the sensitivity can be optimized. This may sometimes require the use of a calibrating dose of analyte for each measurement (See Example 2 as a means of minimizing drift.)

The present invention also provides an improved method for detecting response to an analyte in which a signal may derived by altering and monitoring dc bias potential, while analyte is binding to the channels during the biosensor gating event, either to maintain the admittance constant preferably at the frequency for minimum phase or similarly to maintain the phase constant preferably at the frequency for minimum phase.

The present invention further provides an improved method for detect the electrode response to analyte in which the signal response is optimized by automatically altering the dc bias potential to obtain maximum sensitivity or minimum drift.

In order that the nature of the present invention maybe more clearly understood the invention will now be described by way of non-limiting example.

EXAMPLE 1

On a clean glass or plastic slide, an adhesion layer of chromium (50 angstrom) followed by a gold layer (200–2000 angstroms) is evaporated. The freshly evaporated sold coated electrode is taken and immediately immersed in an ethanolic solution of linker lipid (FIG. 1) (300 ul of 10 mM), the disulfide of mercaptoacetic acid (150 ul of 10 mM), linker gramicidin (FIG. 2) (150 ul of 0.01 mg/ml, membrane spanning lipid C (FIG. 3) (2.25 ul of 0.1 mM) and membrane spanning lipid D (FIG. 3) (45 ul of 1 mM) in ethanol (50 ml). The gold coated electrode is left immersed in the solution for 5–60 minutes. rinsed with ethanol and assembled into a Teflon slide assemble holder such that an electrode surface is defined by a circular Teflon well pressed onto the gold electrode. The Teflon well forms a tight, water impermeable seal at the electrode perimeter. This procedure forms the first layer of the bilayer sensor membrane and may be stored in ethanol, glycerol, ethylene glycol or other alcohol for several months. Formation of the second layer of the bilayer membrane is carried out by addition of 5 ul of a solution containing 14 mM of diphytlayl phosphatidyl choline/glyceryl diphytanyl ether (7:3 ratio), biotinylated gramicidin (FIG. 4) in a ratio of 100.000:1 (total lipid) :gramicidin. The well assembly was then rinsed twice with phosphate buffered saline (PBS) resulting the formation of the second lipid layer of the bilayer sensing membrane. The well assembly holds approximately 150 ul of PBS. Into this 150 ul of PBS in the well is placed a counter electrode, a connection is made between this counter electrode and the impedance bridge measure apparatus. To complete the electrical circuit, the other connection on is made between the gold electrode and the impedance bridge. In order to control the dc potential offset a reference electrode is inserted into the well also contacting the PBS solution and the potential is controlled such that the gold electrode potential may be varied. The apparatus needed to make such three terminal measurements are known to those skilled in the art. Alternatively, the dc offset may be varied by changing the metal type which makes up the counter electrode. This sets up electrochemical potential between the counter electrode and the gold electrode. A dc offset may also be produced electronically in a two terminal measurement using the impedance bridge the conduction of the membrane may then be determined. Standard Bode plots are shown in FIG. 5. The effect of changing the counter electrode material, thus changing the potential, on gramicidin induced membrane conduction is shown. As can be seen stainless steel and titanium counter electrodes produce more conductive membranes than silver or gold counter electrodes when equivalent membrane sensor electrodes are measured.

Using a three terminal measurement it was found that the gramicidin induced membrane conduction increases as a negative potential is applied to the sensor membrane in the range of between 0 mV to –500 mV. FIG. 6 shows the effect of Long the potential on gramicidin containing membranes. As an indication of conduction the frequency at phase minimum is used. The higher the frequency at phase minimum, the more conductive the membrane. However, on application of a positive potential (0 mV to +50 mV) relative to the gold electrode the gramicidin induced membrane conduction decreased, such that at +200 mV the membrane was ionically insulating.

It is believed that using counter electrode metals such as stainless steel or titanium places a dc offset of between –150 mV to 400 mV on the gold electrode relative to the counter electrode. It has been further found that thereproducibility in terms of conduction for a particular concentration of ionophore in the membrane has been improved from coefficients of variation (cv's) of 30–60% using silver counter electrodes to cv's of 10–15% using stainless steel electrodes.

Similar effects were found if ionophores such as valinomycin were used instead of the gramicidin derivatives.

EXAMPLE 2

A membrane was formed as described above in Example 1. A dc offset across the biosensor membrane was established using a three terminal voltage clamp with a platinum counter electrode, a silver chloride reference electrode and a gold sensing electrode.

FIG. 10 shows the effect of varying the dc offset on the drift in the biosensor output. The output signal was the frequency at minimum phase. The graph Y axis shows the rate of the frequency at minimum phase divided by the initial frequency at minimum phase.

The RC network in FIG. 10 is a representation of the passive electrical properties of the sensor membrane. This model consists of two capacitors connected in series, one with a value of 0.1 microFarad and the second with a value of 0.01 microFarad and a resistor of about 300 kilOhm connected in parallel with the 0.01 microFarad capacitor. When this network was connected to the measuring apparatus the intrinsic drift in the apparatus was found to be negligible as is indicated in. FIG. 10.

It will be appreciated by persons skilled in the art that numerous variations and/or modifications may be made to the invention as shown in the specific embodiments without departing from the spirit or scope of the invention as broadly described, the present embodiments are, therefore, to be considered in all respect as illustrative and not restrictive.

Figure 1:
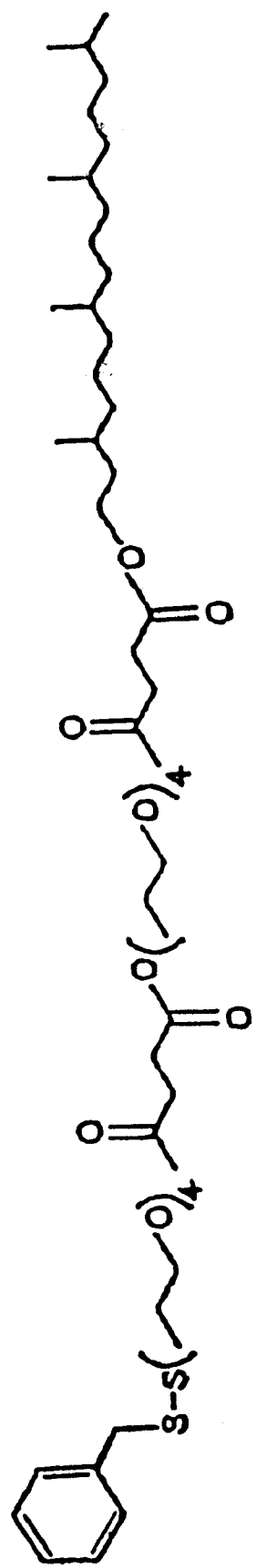
FIG. 1 depicts the structural formula for a linker lipid.

What is claimed is:

1. An improved membrane based biosensor comprising a lipid membrane incorporating ionophores, the conductivity of the lipid membrane being dependent on the presence or absence of an analyte, a reference electrode, a sensing electrode onto which is deposited the lipid membrane such that a functional reservoir exists between the lipid membrane and the sensing electrode, the improvement comprising including in the biosensor means to apply a dc electrical potential offset to the sensing electrode relative to the reference electrode, said dc electrical potential offset being produced by a counter electrode.

2. An improved membrane based biosensor according to claim 1, wherein the means to apply a dc electrical potential is a means capable of applying a dc electrical potential of between +500 mV to −500 mV the sensing electrode.

3. An improved membrane based biosensor according to claim 1, wherein the electrochemical potential between the counter electrode and the sensing electrode produces an electrical potential of between 0 to −500 mV, with the sensing electrode being at the negative potential.

4. An improved membrane based biosensor according to claim 1, wherein the counter electrode is made from stainless steel.

5. An improved membrane based biosensor according to claim 1, wherein the counter electrode is made from titanium.

6. An improved membrane based biosensor according to claim 1, wherein the counter electrode is made from metallic element selected from the group consisting of silver, gold, platinum, palladium, copper, chromium, or molybdenum.

7. An improved membrane based biosensor according to claim 1, wherein the counter electrode is made from a metal that is capable of being deposited in a thin film onto a plastic, glass or silicon substrate, said metal being stable for at least 30 minutes in aqueous solution and sets up the appropriate electrochemical potential relative to the sensing electrode on addition of an aqueous solution.

8. An improved membrane based biosensor according to claim 1, wherein the counter electrode is an electrochemically neutral metal relative to the sensing electrode and the dc electrical potential of between +500 mV to −500 mV is created by electronic means.

9. An improved membrane based biosensor according to claim 1, wherein the counter electrode produces an electrochemical potential relative to the sensing electrode which is enhanced or negated or reversed using a dc electrical potential created by electronic means to give a potential of between +500 mV to −500 mV.

10. An improved membrane based biosensor according to claim 1, wherein the dc offset potential at the sensing electrode, onto which is deposited a lipid membrane, is controlled using a three terminal measurement, wherein the impedance measurement is made between the counter electrode and the working electrode which is the sensing electrode and where the dc offset potential is controlled by a reference electrode to be between +500 mV to −500 mV as required.

11. An improved membrane based biosensor according to claim 10, wherein the sensing electrode comprises a metal.

12. An improved membrane based biosensor according to claim 11, wherein the metal used for the sensing electrode is a layer of freshly evaporated, sputtered, plasma etched or ion beam milled gold.

Figure 2:
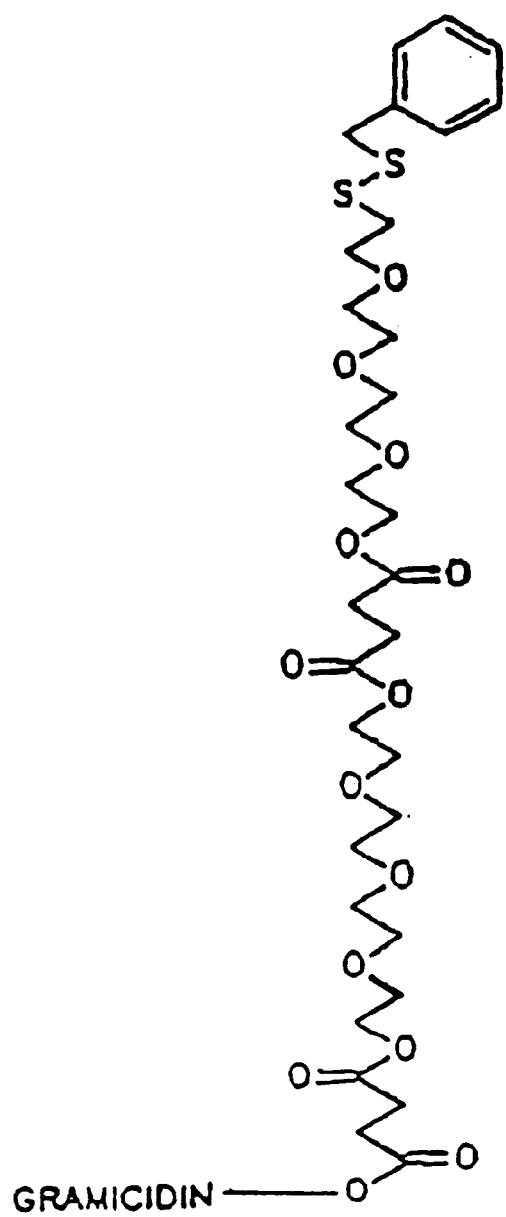
FIG. 2 depicts the structural formula for the linker Gramicid.
Figure 3:
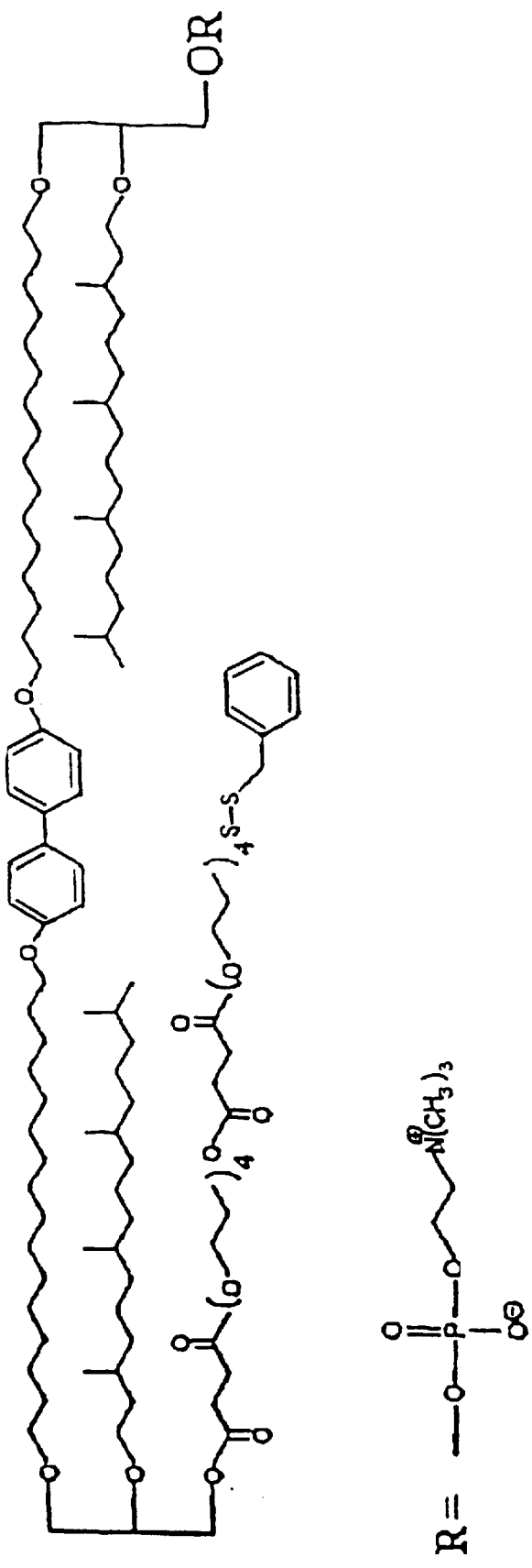
FIG. 3 depicts the structural formulae for membrane spanning lipids.
Figure 3:
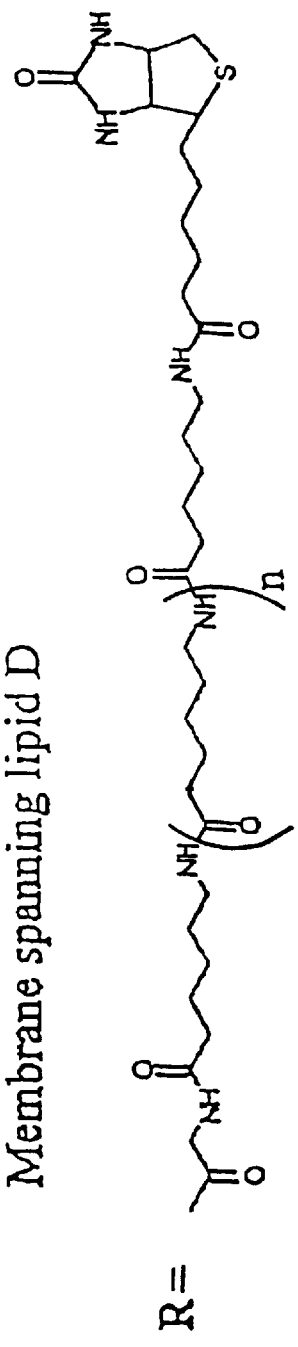

13. An improved membrane based biosensor according to claim 1, wherein the lipid membrane comprises a first layer of linker lipid (FIG. 1), the disulfide of mercaptoacetic acid, linker gramicidin (FIG. 2), membrane spanning lipid C (FIG. 3) and membrane spanning lipid D (FIG. 3).

Figure 4:
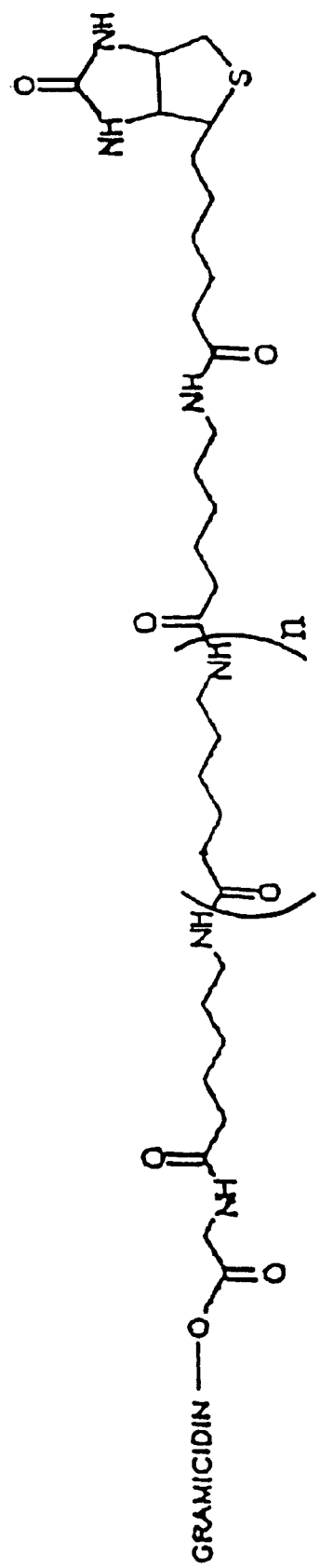
FIG. 4 depicts the structural formula for Biotinylated Gramicidin.
Figure 5A:
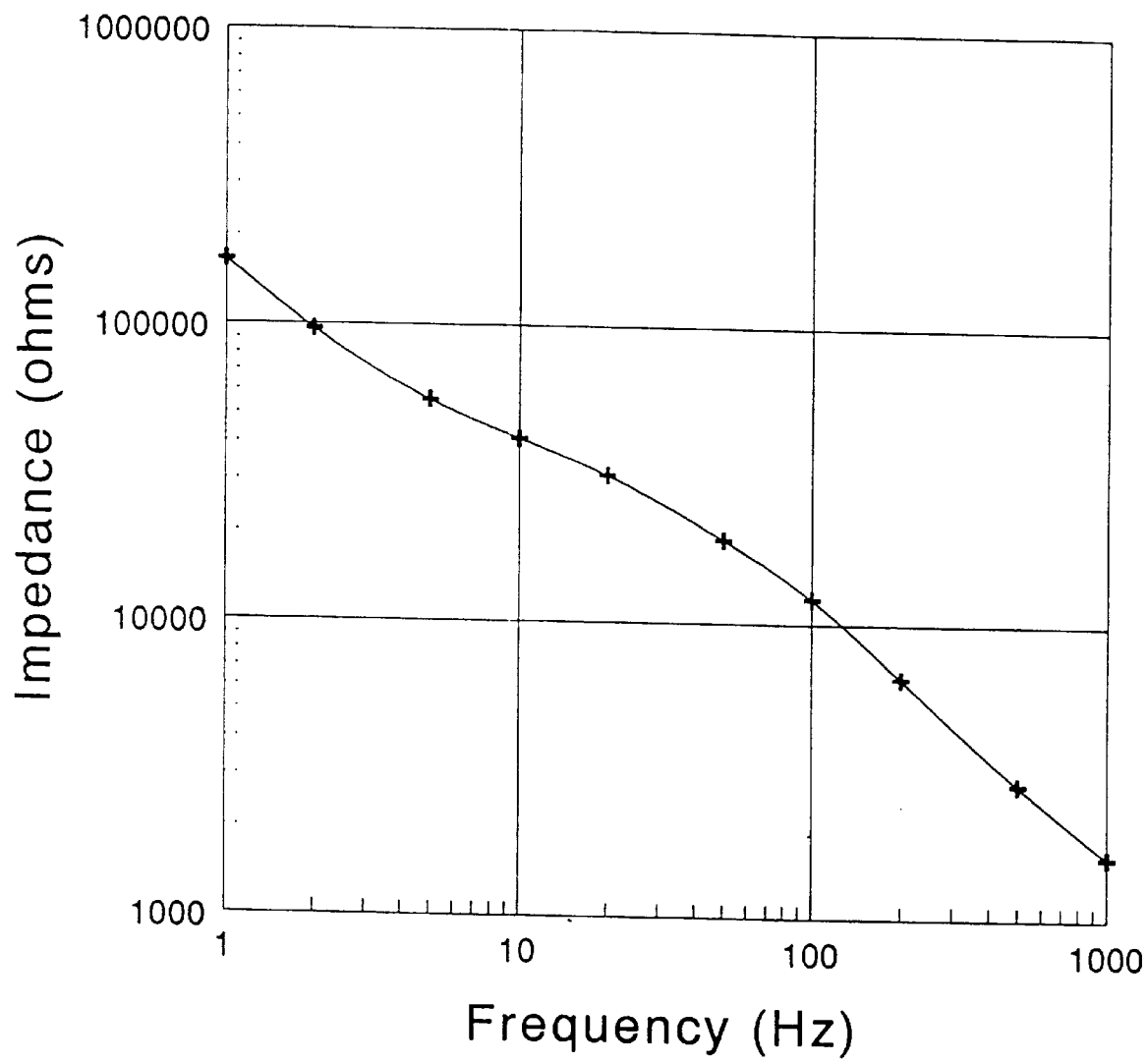
FIG. 5A is a graph of impedance as a function of frequency for silver counter electrodes.
Figure 5B:
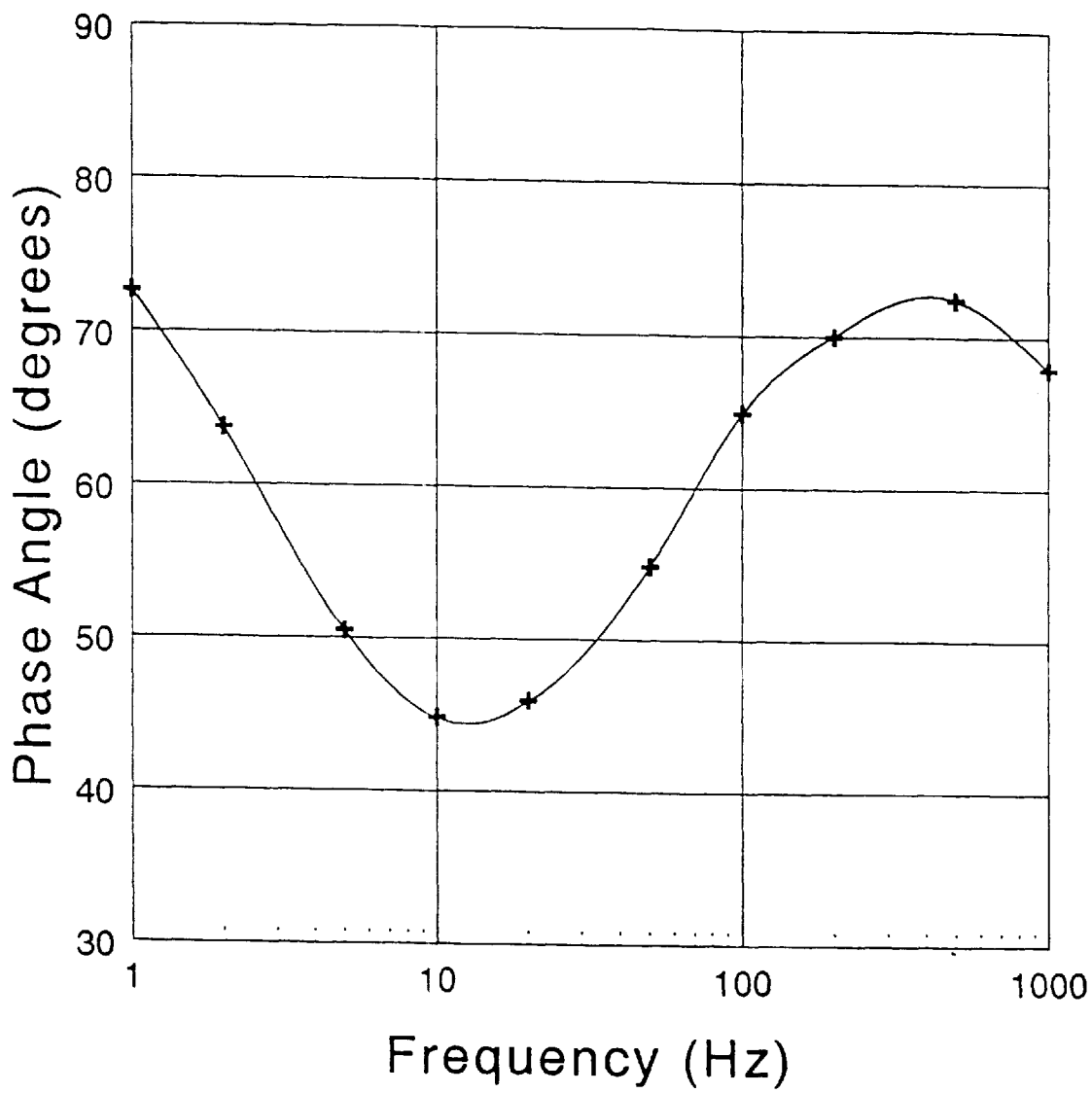
FIG. 5B is a graph of phase as a function of frequency for silver counter electrodes.
Figure 5C:
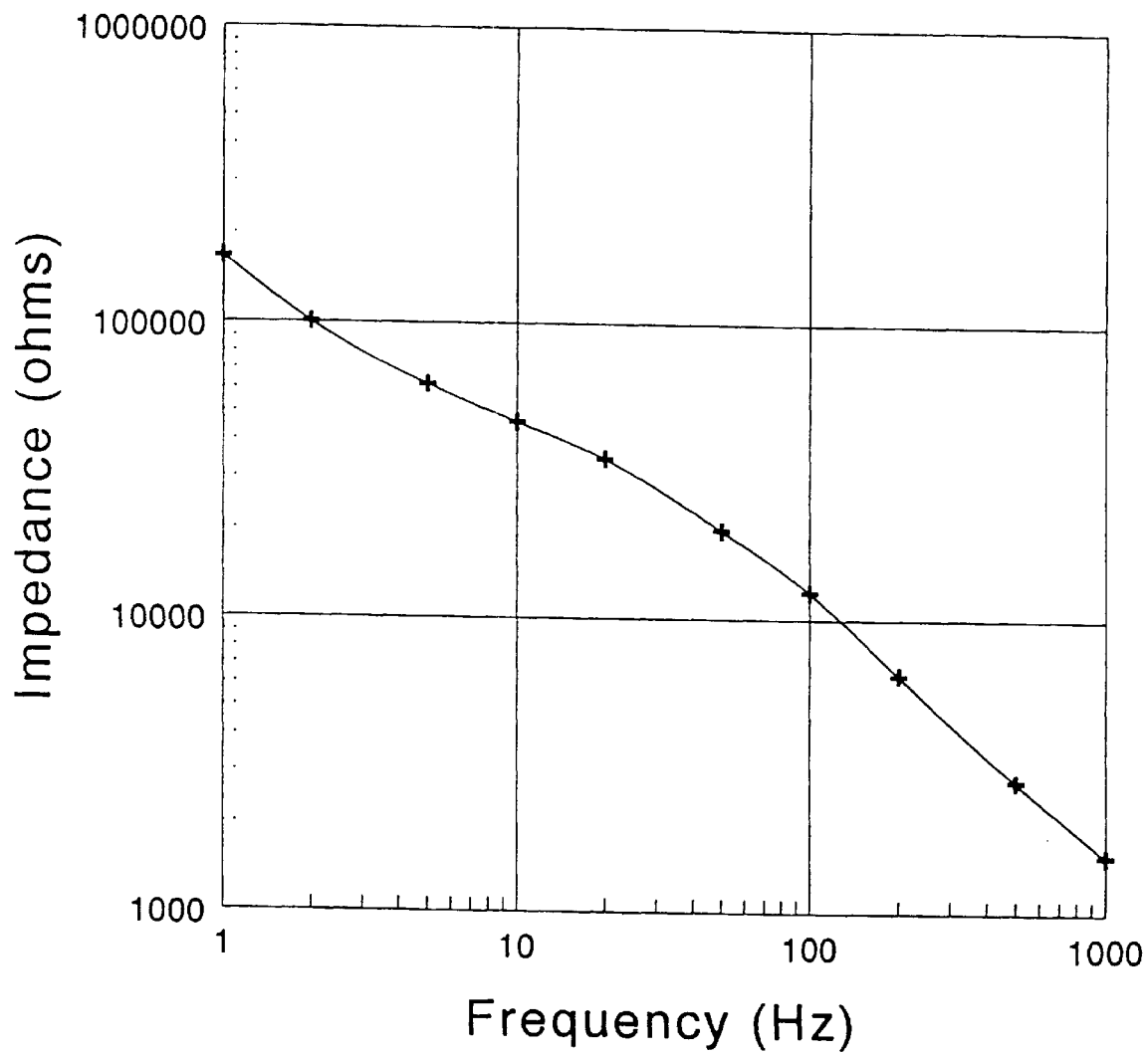
FIG. 5C is a graph of impedance as a function of frequency for gold counter electrodes.
Figure 5D:
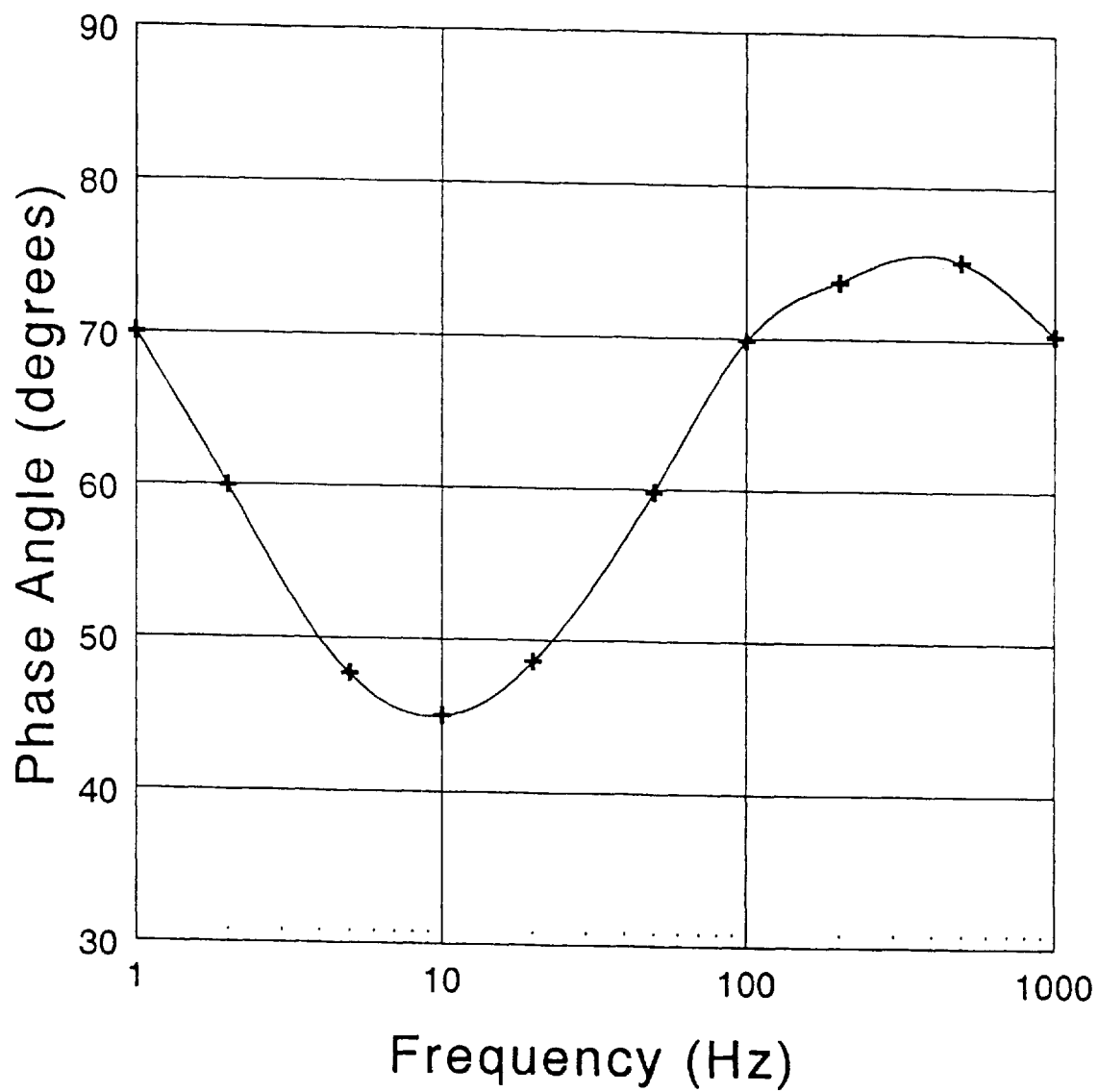
FIG. 5D is a graph of phase as a function of frequency for gold counter electrodes.
Figure 5E:
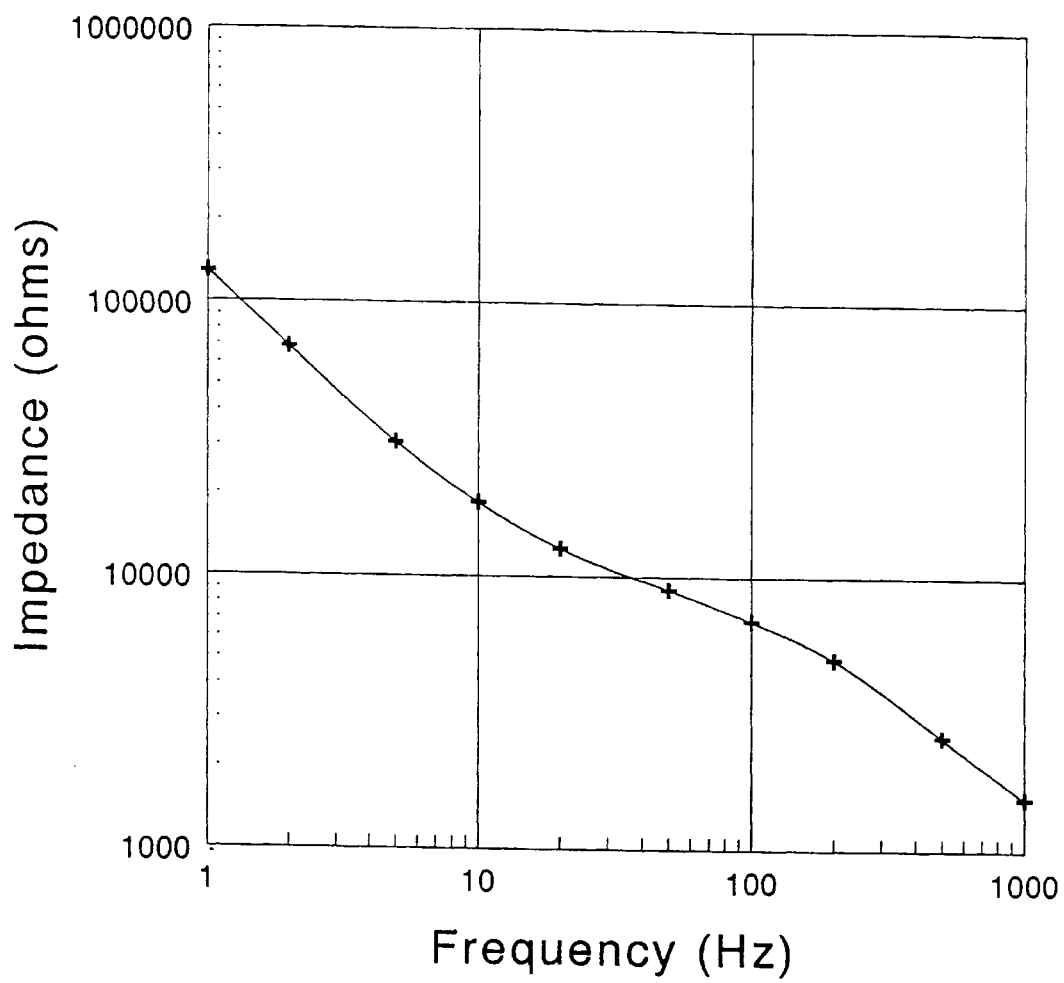
FIG. 5E is a graph of impedance as a function of frequency for stainless steel counter electrodes.
Figure 5F:
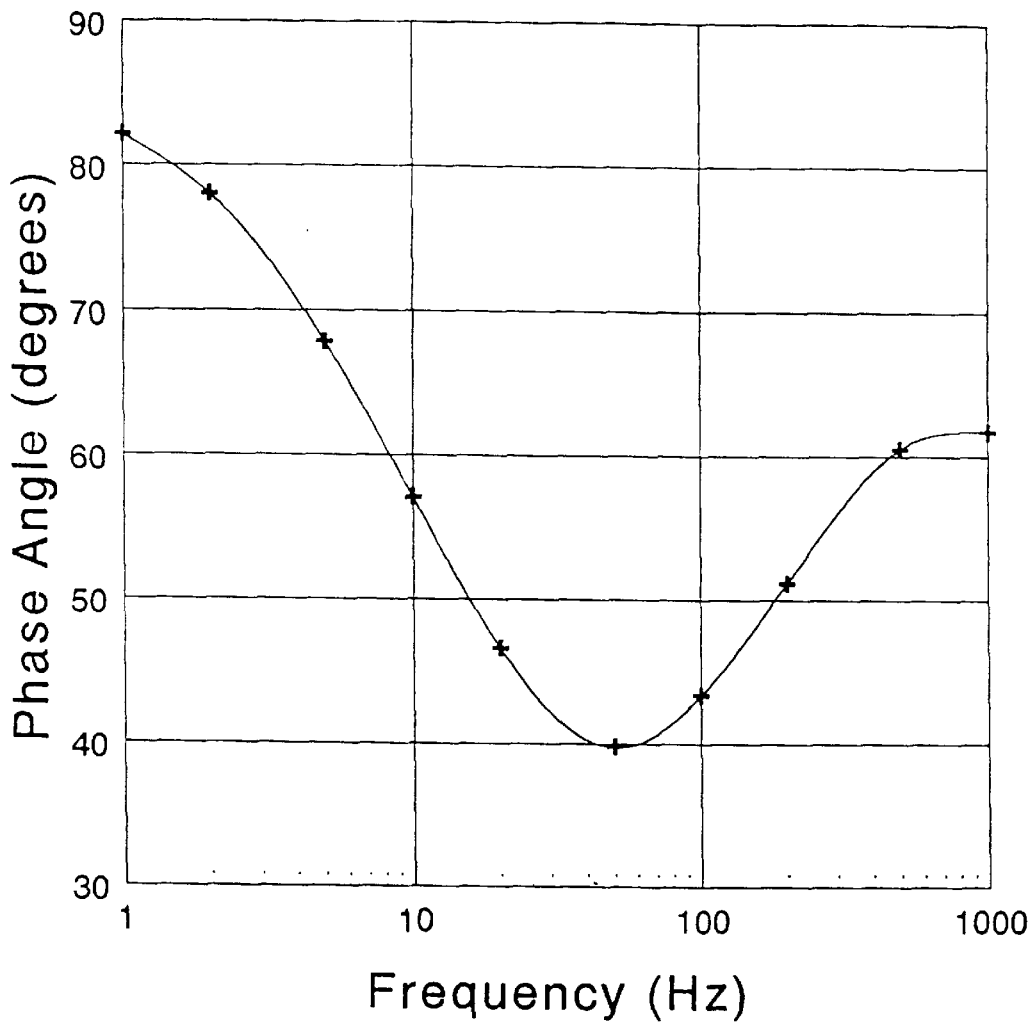
FIG. 5F is a graph of phase as a function of frequency for stainless steel counter electrodes.
Figure 5G:
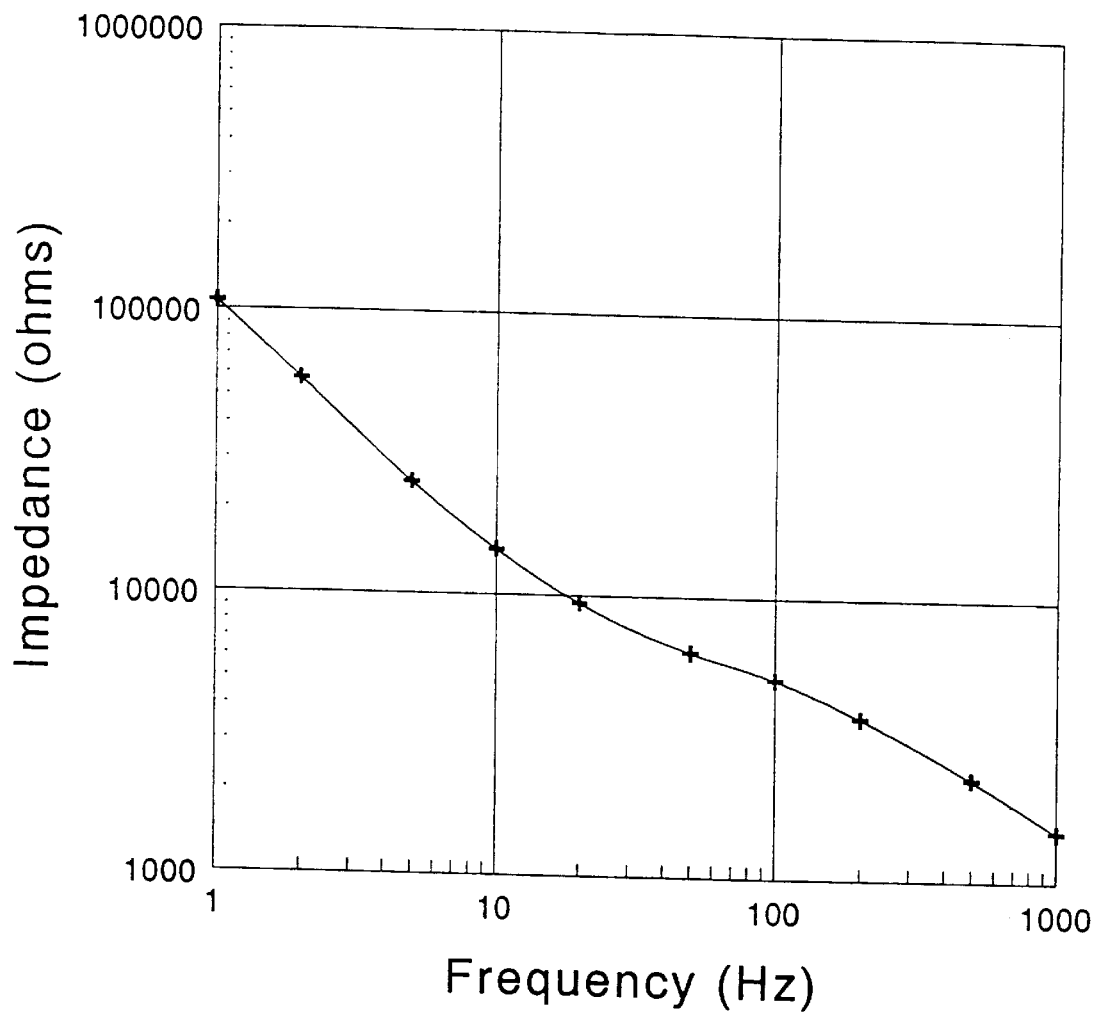
FIG. 5G is a graph of impedance as a function of frequency for titanium counter electrodes.
Figure 5H:
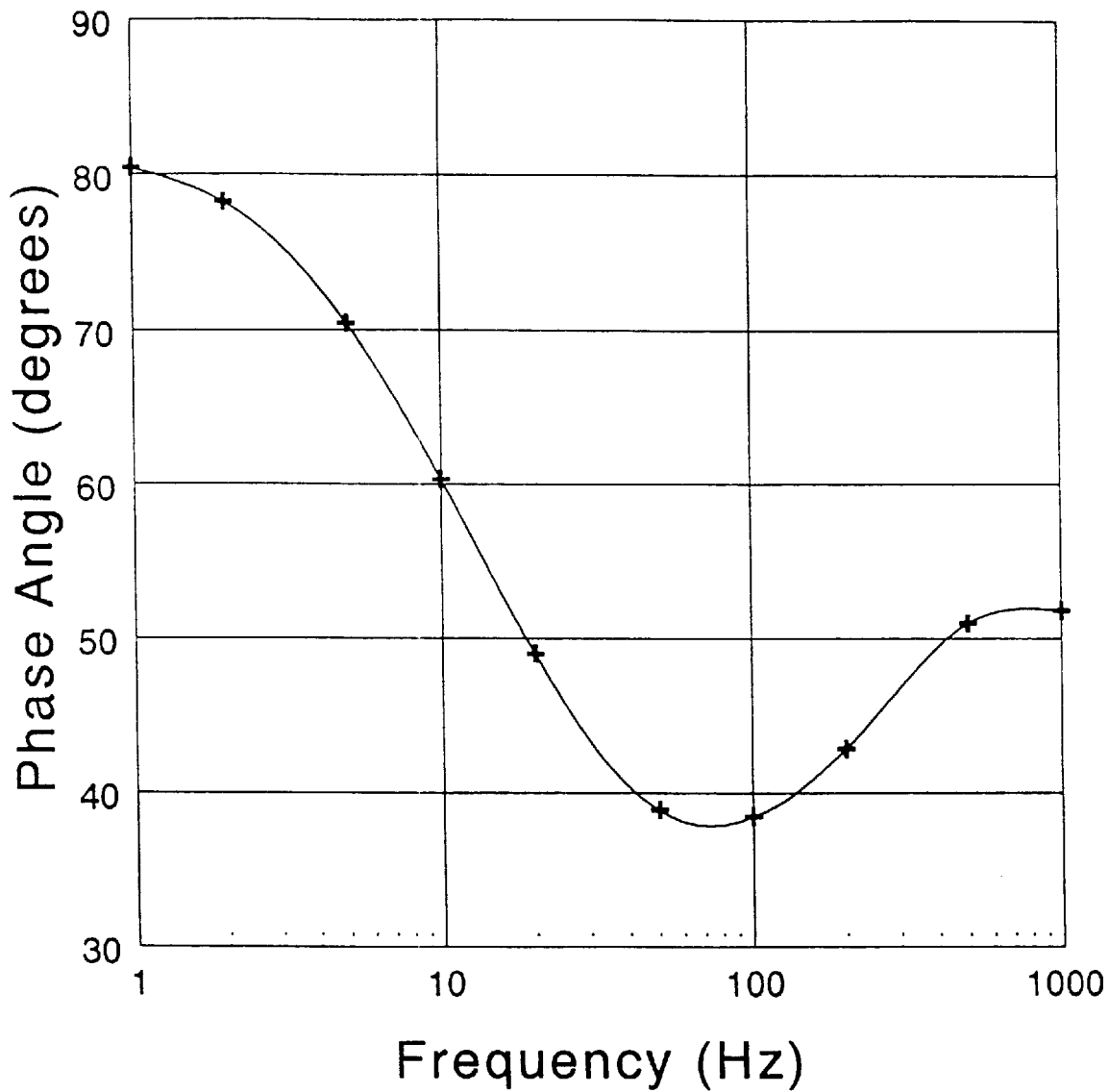
FIG. 5H is a graph of phase as a function of frequency for titanium counter electrodes.
Figure 6:
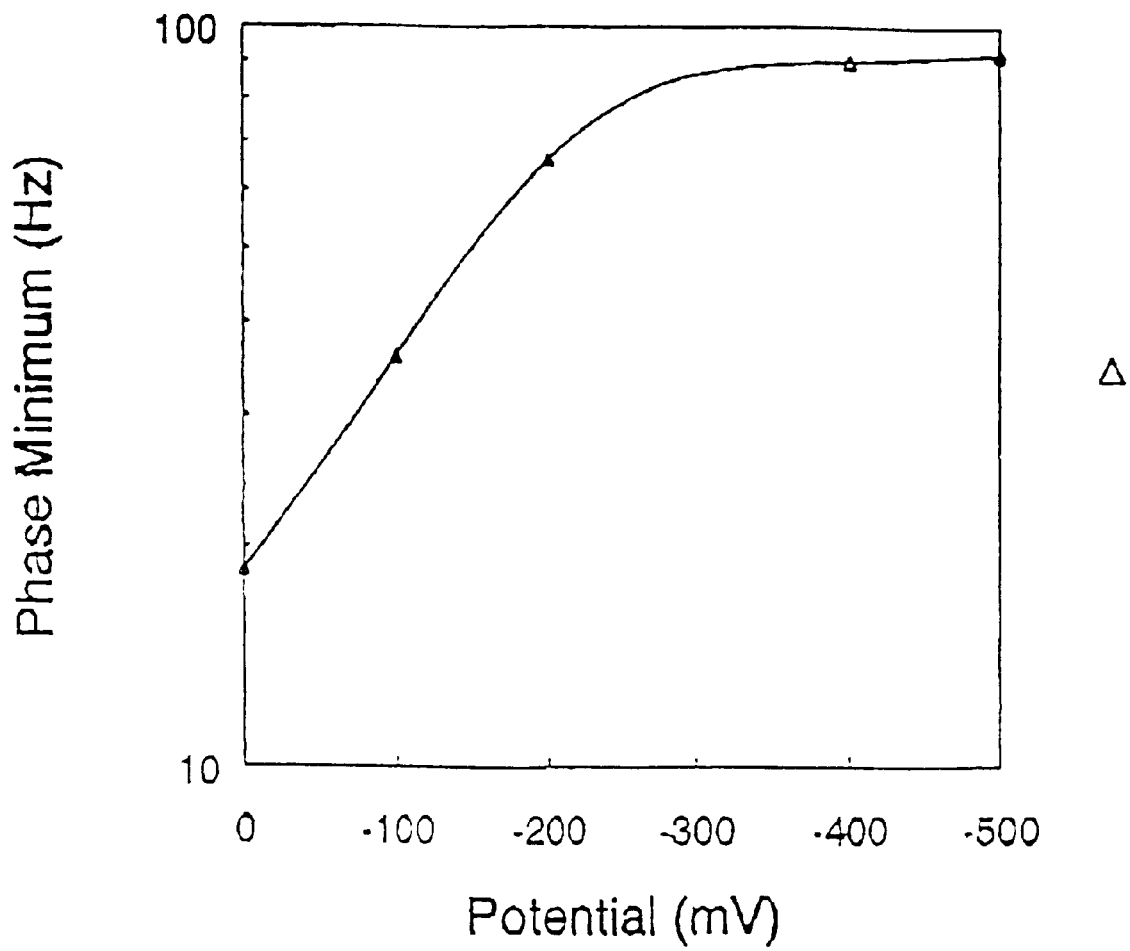
FIG. 6 is a graph of conduction at minimum phase as a function of potential for a three terminal bridge.
Figure 7:
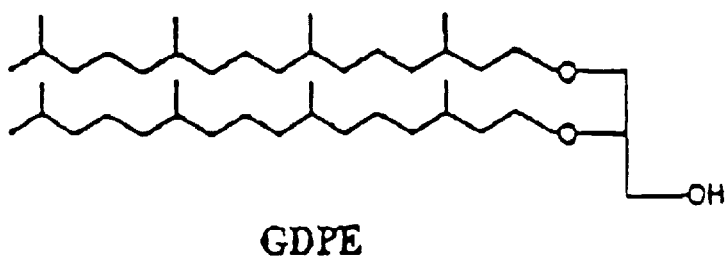
FIG. 7 depicts the structure formulae for GDPE and DPEPC.
Figure 7:
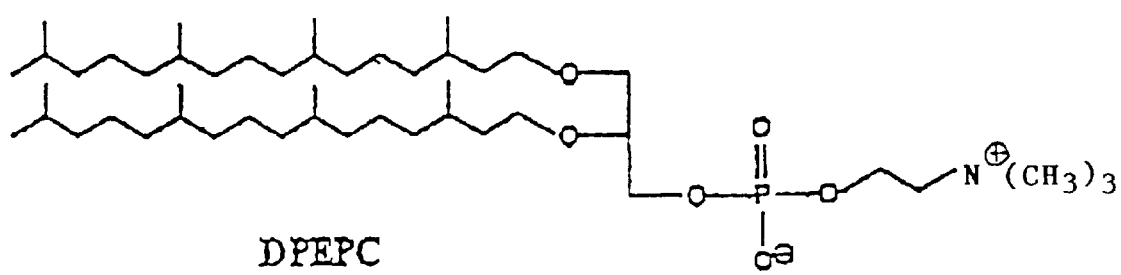
Figure 8A:
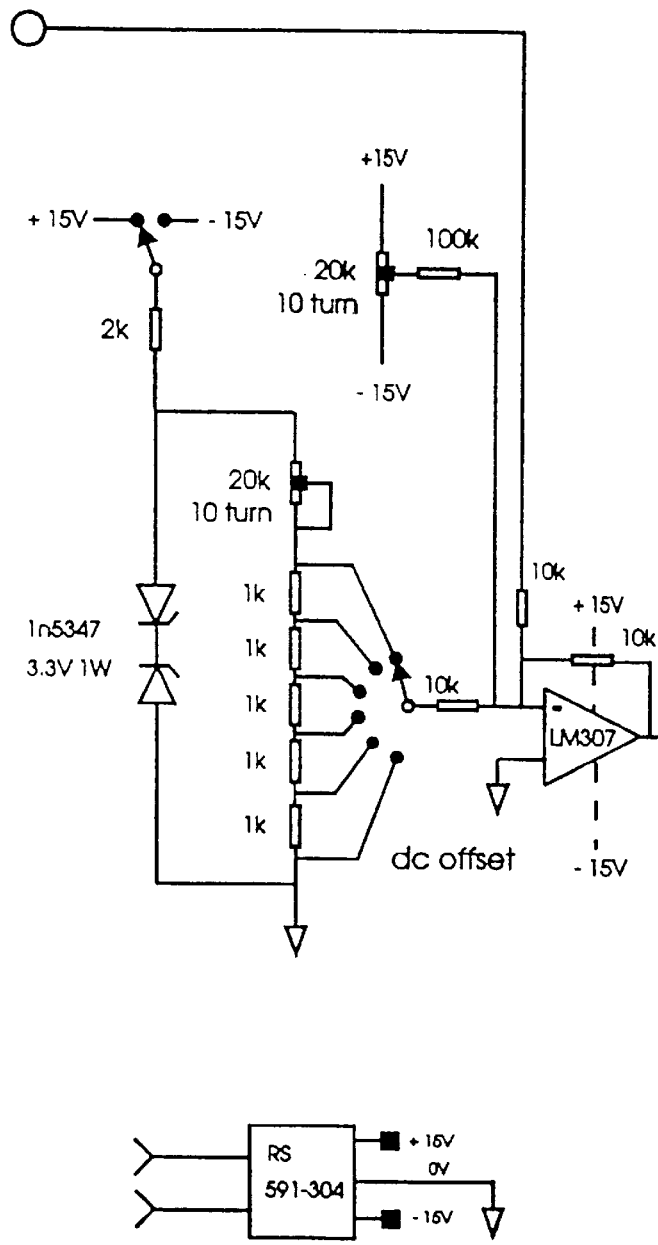
FIG. 8A is a schematic diagram of a portion of the circuit of the present invention.
Figure 8B:
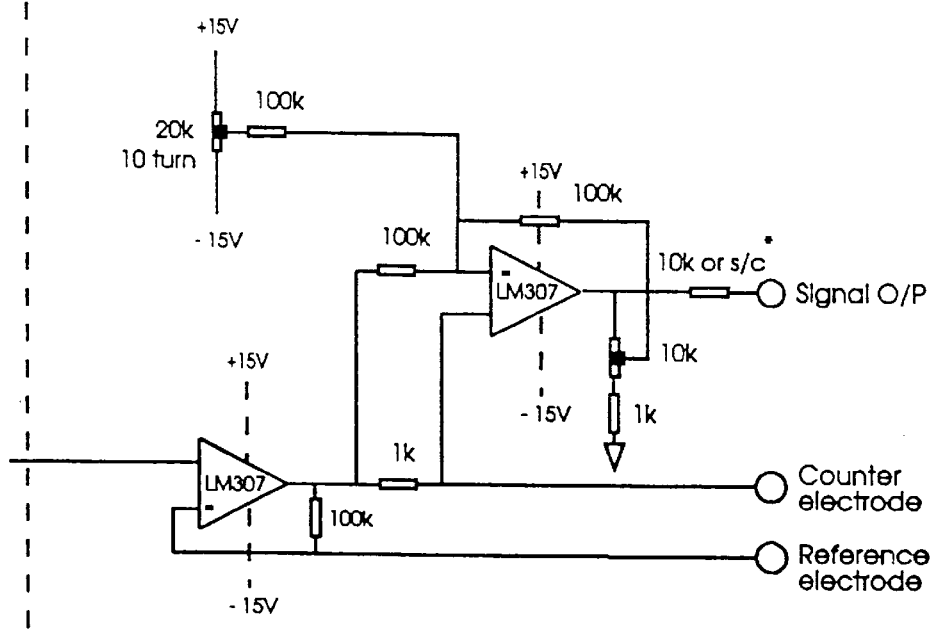
FIG. 8B is a schematic diagram of a further portion of the circuit of the present invention.
Figure 9A:
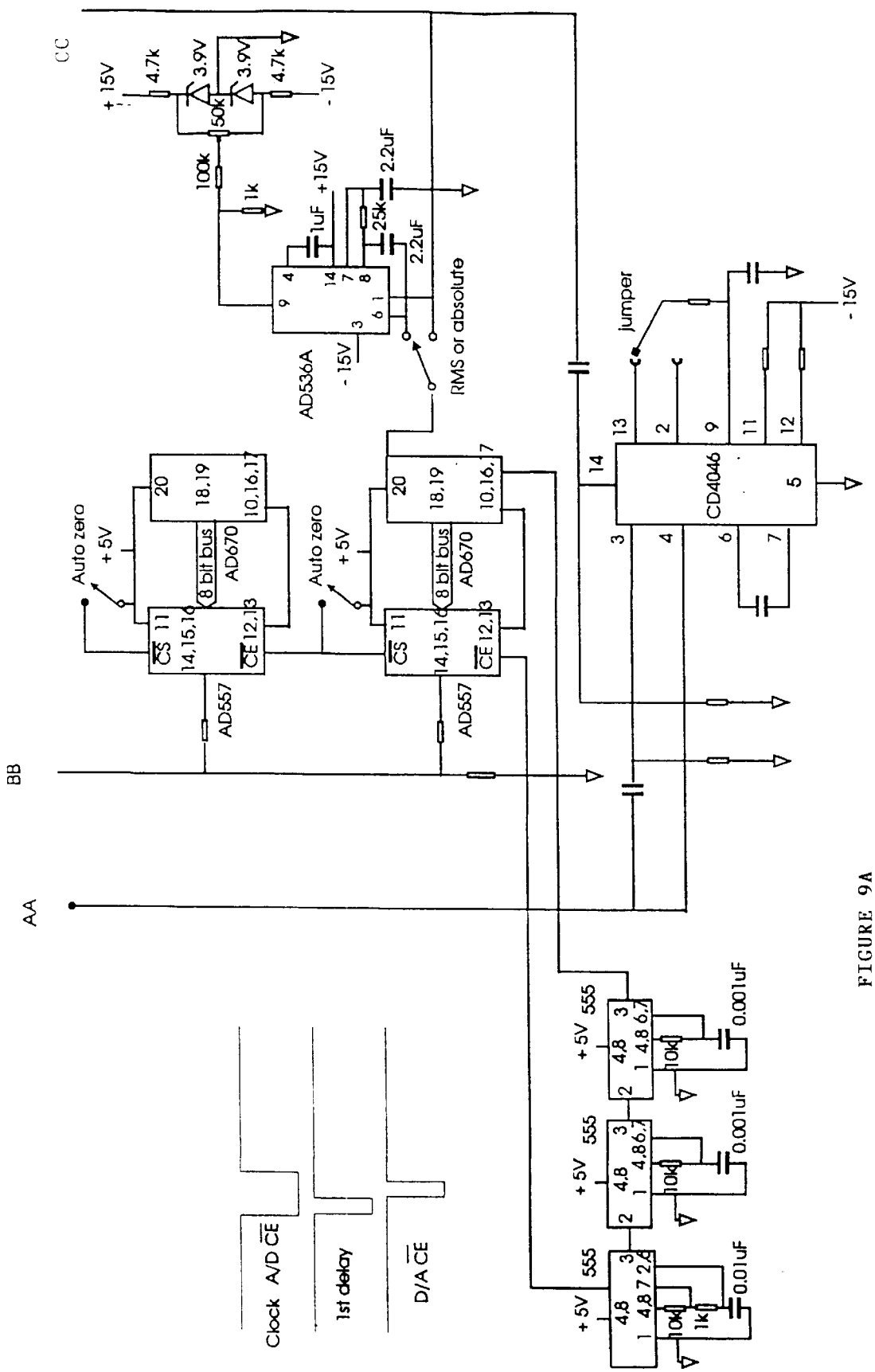
FIG. 9A is a schematic diagram of the logic components of the present invention.
Figure 9B:
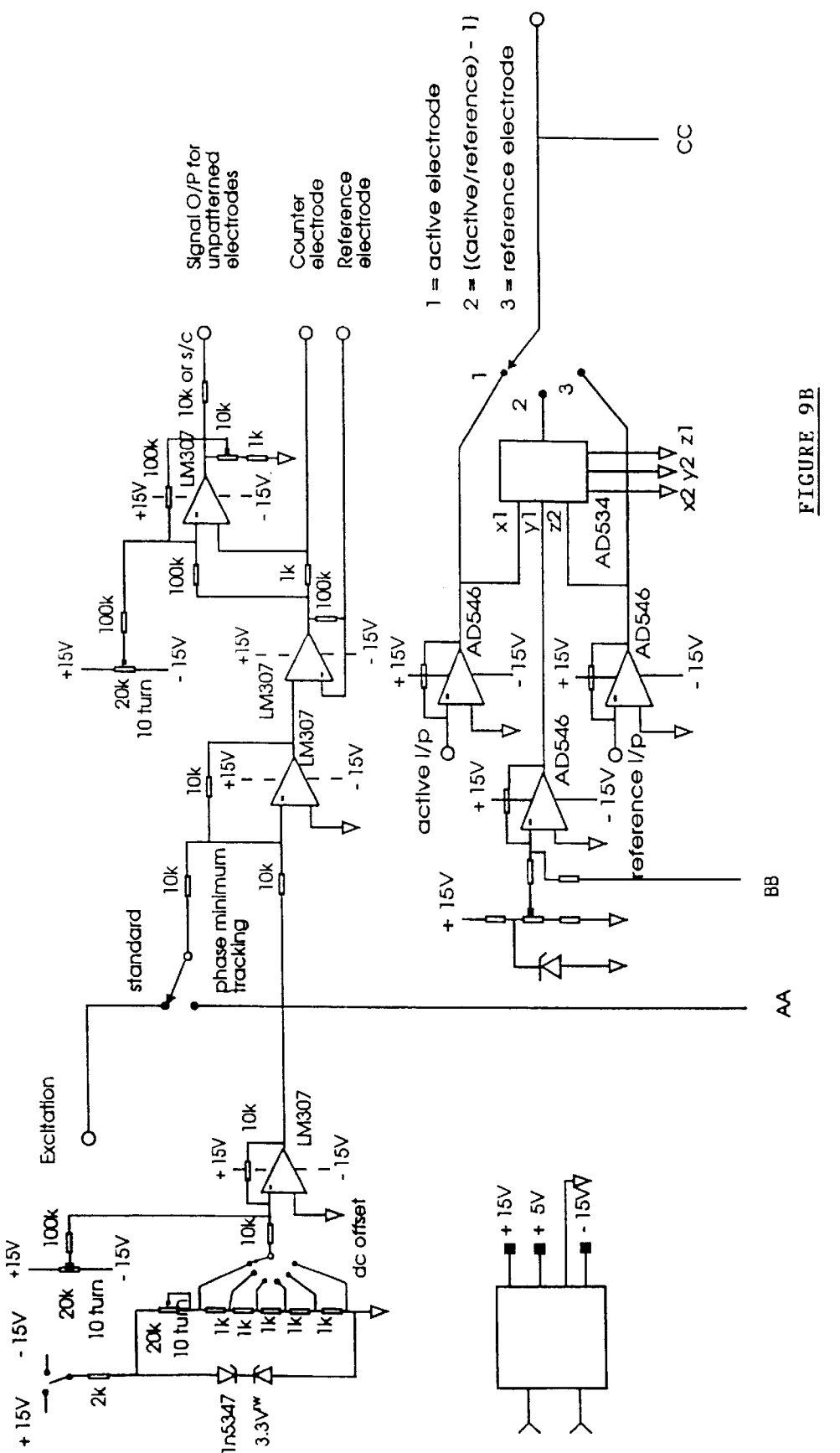
FIG. 9B is a schematic diagram of the electrical components of the present invention.
Figure 10:
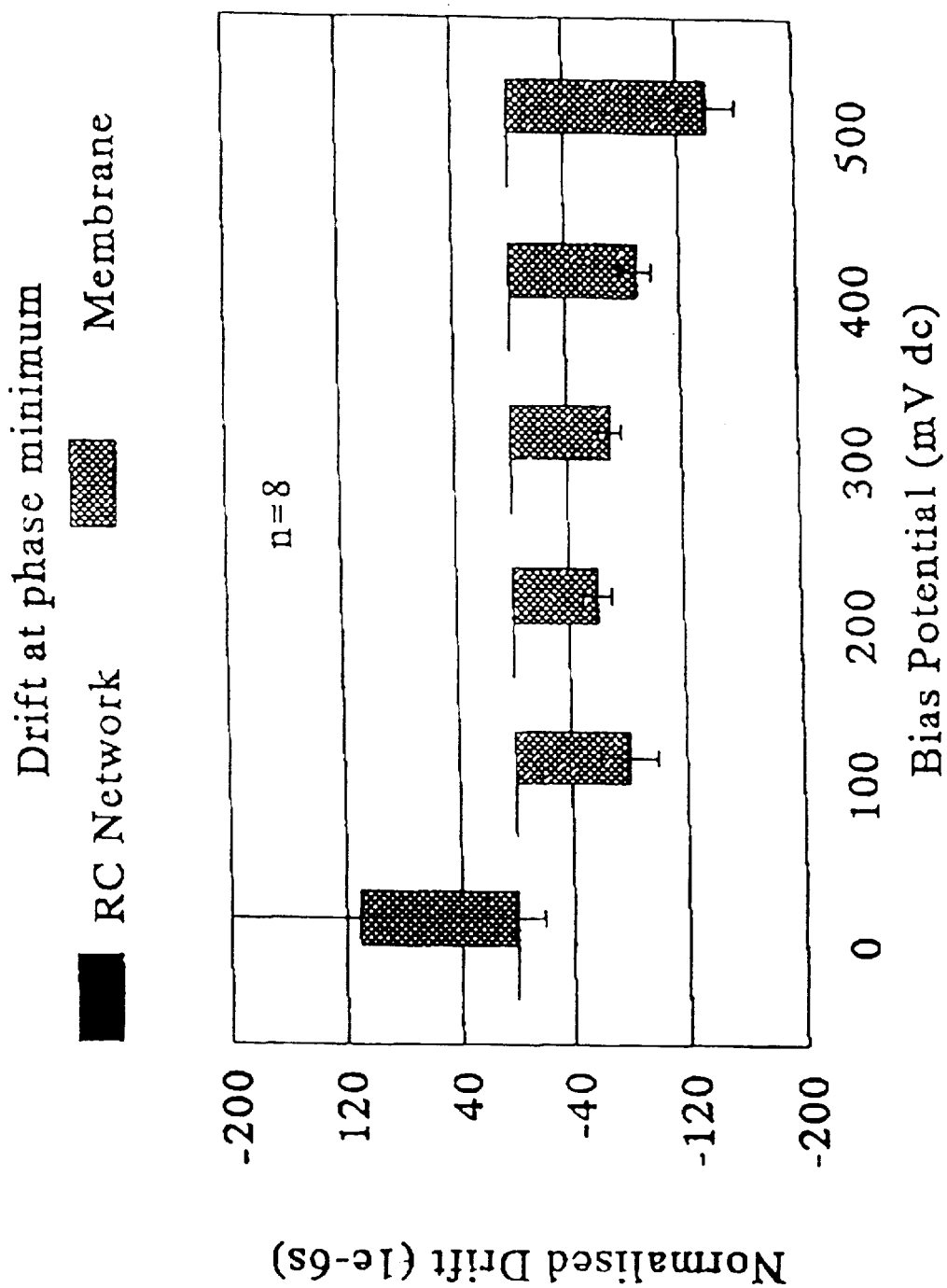
FIG. 10 is a representation of the passive electrical properties of the sensor membrane.

14. An improved membrane based biosensor according to claim 13, wherein the lipid membrane comprises a second layer of diphytanyl phosphatidyl choline, glycerol, diphytanyl ether, and biotinylated gramicidin (FIG. 4).

15. An improved membrane based biosensor according to claim 14, wherein the said second layer contains at least a proportion of a phosphatidyl choline, or phosphatidyl ethanolamine or phosphatidic acid lipid.

16. An improved membrane based biosensor according to claim 14 wherein said second layer contains at least a proportion of a charged lipid.

17. An improved membrane based biosensor according to claim 11, wherein the lipid membrane is a monolayer.

18. An improved method detecting the presence or absence of an analyte in a sample using a membrane based biosensor comprising a lipid membrane incorporating ionophores, the conductivity of the lipid membrane being dependent on the presence or absence of the a reference electrode, a sensing electrode onto which is deposited the lipid membrane such that a functional reservoir exists between the lipid membrane and the sensing electrode, the improvement comprising applying a dc electrical potential offset to the sensing electrode relative to the reference electrode, said dc electrical potential offset being produced by a counter electrode.

19. An improved method according to claim 18, wherein a dc electrical potential of between +500 mV to −500 mV is applied to the sensing electrode.

20. An improved method according to claim 18, wherein the electrochemical potential between the counter electrode and the sensing electrode produces an electrical potential of between 0 to −500 mV, with the sensing electrode being at the negative potential.

21. An improved method according to claim 18, wherein the counter electrode is made from stainless steel.

22. An improved method according to claim 18, wherein the counter electrode is made from titanium.

23. An improved method according to claim 18, wherein the counter electrode is made from metallic element selected from the group consisting of silver, gold, platinum, palladium, copper, chromium or molybdenum.

24. An improved method according to claim 18, wherein the counter electrode is made from a metal that is capable of being deposited in a thin film onto a plastic, glass or silicon substrate, said metal being stable for at least 30 minutes in aqueous solution and sets up the appropriate electrode chemical potential relative to the sensing electrode on addition of an aqueous solution.

25. An improved membrane based biosensor according to claim 18, wherein the counter electrode is an electrochemically neutral metal relative to the sensing electrode and the dc electrical potential of between +500 mV b −500 mV is created by electronic means.

26. An improved membrane based biosensor according to claim 18, wherein the counter electrode produces an electrochemical potential relative to the sensing electrode which is enhanced or negated or reversed using a dc electrical potential created by electronic mans to give a potential of between +500 mV to −500 mV.

27. An improved membrane based biosensor according to claim 18, wherein the dc offset potential at the sensing electrode, onto which is deposited a lipid membrane, is controlled using a three terminal measurement, wherein the impedance measurement is made between the counter electrode and the working electrode which is the sensing electrode and where the dc offset potential is controlled by a reference electrode to be between +500 mV to −500 mV as required.

28. An improved membrane based biosensor according to claim 18, wherein the sensing electrode comprises metal.

29. An improved method according to claim 28, wherein the metal used for the sensing electrode is a layer of freshly evaporated, sputtered, plasma etched or ion beam milled old.

30. An improved method according to any one of claims 18, wherein the lipid membrane comprises a first layer of linker lipid (FIG. 1), the disulfide of mercaptoacetic acid, linker gramicidin (FIG. 2), membrane spanning lipid C (FIG. 3) and membrane spanning lipid D (FIG. 3).

31. An improved method according claim 30, wherein the lipid membrane comprises a second layer diphytanyl phosphatidyl choline, glycerol diphytanyl ether, and biotinylated gramicidin (FIG. 4).

32. An improved membrane based biosensor according to claim 31, wherein the said second layer contains at least a proportion of a phosphatidyl choline, or phosphatidyl ethanolae or phosphatidic acid lipid.

33. An improved membrane based biosensor according to claim 31, wherein said second layer contains at least a proportion of a charged lipid.

34. An improved membrane based biosensor according to claim 18, wherein the sensing membrane is a monolayer.

* * * * *

UNITED STATES PATENT AND TRADEMARK OFFICE
CERTIFICATE OF CORRECTION

PATENT NO.    : 6,451,196 B1
DATED         : September 17, 2002
INVENTOR(S)   : Peter Damien John Osman et al.

It is certified that error appears in the above-identified patent and that said Letters Patent is hereby corrected as shown below:

<u>Title page, Item [54] and Column 1, line 3,</u>
Change "IONIC RESERVOIR THROUGH APPICATION OF AN ELECTRICAL POTENTIAL" to -- IMPROVEMENT IN AN IONIC RESERVOIR THROUGH APPLICATION OF AN ELECTRICAL POTENTIAL --;

Signed and Sealed this

Sixteenth Day of September, 2003

JAMES E. ROGAN
*Director of the United States Patent and Trademark Office*